United States Patent
Karlinsey

(10) Patent No.: US 9,974,717 B2
(45) Date of Patent: May 22, 2018

(54) PHOSPHATE COMPOSITION FOR DENTAL STRENGTHENING

(71) Applicant: Robert L Karlinsey, Indianapolis, IN (US)

(72) Inventor: Robert L Karlinsey, Indianapolis, IN (US)

(*) Notice: Subject to any disclaimer, the term of this patent is extended or adjusted under 35 U.S.C. 154(b) by 53 days.

(21) Appl. No.: 14/092,023

(22) Filed: Nov. 27, 2013

(65) Prior Publication Data

US 2014/0086850 A1    Mar. 27, 2014

Related U.S. Application Data

(63) Continuation-in-part of application No. 13/555,673, filed on Jul. 23, 2012.

(60) Provisional application No. 61/839,334, filed on Apr. 27, 2012.

(51) Int. Cl.

| | |
|---|---|
| *A61Q 11/00* | (2006.01) |
| *A61K 8/24* | (2006.01) |
| *A61K 33/06* | (2006.01) |
| *A61K 6/00* | (2006.01) |
| *A61K 8/02* | (2006.01) |
| *A61K 8/19* | (2006.01) |

(52) U.S. Cl.
CPC ............ *A61K 6/007* (2013.01); *A61K 6/0082* (2013.01); *A61K 8/0216* (2013.01); *A61K 8/19* (2013.01); *A61K 8/24* (2013.01); *A61K 33/06* (2013.01); *A61Q 11/00* (2013.01)

(58) Field of Classification Search
CPC ........ A61Q 11/00; A61K 8/0216; A61K 8/24; A61K 9/0053; A61K 33/06; A61K 33/42; A23V 2200/312
See application file for complete search history.

(56) References Cited

U.S. PATENT DOCUMENTS

| | | | | |
|---|---|---|---|---|
| 4,183,915 | A | * | 1/1980 | Gaffar .................. A61K 8/21 424/49 |
| 4,353,892 | A | | 10/1982 | Caslavsky et al. |
| 5,571,502 | A | * | 11/1996 | Winston ................ A61K 8/19 424/49 |
| 8,198,779 | B2 | | 6/2012 | Noda |
| 2003/0003219 | A1 | * | 1/2003 | Day et al. .................... 426/660 |
| 2007/0237725 | A1 | * | 10/2007 | Tancredi ............... A23G 3/362 424/48 |
| 2007/0275119 | A1 | * | 11/2007 | Lakkis ........................... 426/3 |
| 2008/0160086 | A1 | * | 7/2008 | Farber ................ A61K 9/0056 424/488 |

* cited by examiner

*Primary Examiner* — Lezah Roberts

(74) *Attorney, Agent, or Firm* — C. John Brannon; Brannon Sowers & Cracraft PC

(57) ABSTRACT

A dentition strengthening delivery system having separate phosphate and calcium salts derived from separate source in a semisolid comestible matrix. The ratio of phosphate to calcium is at least 1:1, and the phosphate concentration is between about 10 ppm to about 10,000 ppm.

9 Claims, No Drawings

PHOSPHATE COMPOSITION FOR DENTAL STRENGTHENING

CROSS-REFERENCE TO RELATED APPLICATIONS

This utility patent application is a continuation-in-part of the co-pending patent application Ser. No. 13/555,673 filed on Jul. 23, 2012, which claimed priority to the then U.S. provisional patent application Ser. No. 61/839,334, filed on Apr. 27, 2012.

TECHNICAL FIELD

This novel technology relates generally to the field of chemistry and, more specifically, to a chemical composition for strengthening dentition.

BACKGROUND

Tooth strengthening, and/or remineralization, naturally occurs through the deposition of salivary minerals such as calcium and phosphate into dentition.

It has been realized that the addition of fluoride can expedite the remineralization process. Additionally, the chemical interaction of fluoride with tooth mineral yields a benefit enjoyed by fluoridated enamel in that fluoridated enamel is less soluble than non-fluoridated enamel and thus more durable. Therefore, fluoridation continues to be an effective dental strategy against mineral loss. Nevertheless, statistics continue to reveal that tooth decay remains problematic. Thus, improving remineralization and/or strengthening remains a challenging problem and opportunity.

Nevertheless, while the above-mentioned approaches may provide benefits, tooth decay remains problematic. Often, combination systems do not provide sufficient mineral integration with the tooth. One reason is due to the undesirable interactions between calcium and fluoride that can occur in an aqueous dental preparation. Often, dental preparations are designed to be compartmentalized or prepared in the absence of water to reduce the unwanted calcium-fluoride or calcium-phosphate interactions during shelf-life. The delivery systems of such products remain ineffective. The underlying reasons for such delivery system designs can be attributed to the interactions due to the presence of water. Marginal remineralization and/or strengthening is one drawback from some of the calcium and phosphate-based preparations that combine the two salts in an aqueous preparation, or a separate preparation in the absence of water. Additionally, the limited remineralization that does occur may break down, rendering the tooth susceptible to repeated acid-attack. Separately, the use of metallic species may not provide acceptable aesthetic or sensory qualities, and may contribute elevated risk factors for patient populations prescribed with certain medications.

Thus, there remains a need for a system that provides for sufficiently bioavailable amounts of calcium and phosphate together to maximize dentition strengthening. The present novel technology addresses this need.

DETAILED DESCRIPTION

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated technology and such further applications of the principles of the novel technology as illustrated therein being contemplated as would normally occur to one skilled in the art to which the novel technology relates.

Tooth mineral is largely constructed of apatite, typically having a calcium to phosphate ratio of about 5:3. As practiced and taught throughout dentistry, the combination of calcium and phosphate are both critical to tooth structure, and it is considered axiomatic to strive for regularly restoring calcium and phosphate lost due to acid attacks and/or physical attrition. Physiologically, these minerals are naturally supplied by the saliva. However, supplements or additional mineralizing dental preparations containing calcium and phosphate may also provide increased concentrations of these minerals to the dentition.

Discussions surrounding mineralization, remineralization, and the like customarily include both calcium and phosphate, and not one mineral without the other; that is, calcium and phosphate are typically discussed in conjunction. If calcium and phosphate are discussed separately, calcium is generally considered the most important species, since fluoride and phosphate and carbonate and hydroxide ions readily coordinate with calcium to produce mineralization. It is conventional wisdom that the composition of mineral lost in typical carious lesions in human enamel is largely comprised of between about 30% and about 40% calcium content. In stark contrast, between 13 and 18.5% phosphorous content is lost, which is about half of the content of calcium lost. It has been demonstrated that a 5:3 calcium to phosphate ratio remineralized softened enamel more effectively relative to a calcium to phosphate ratio of 1:1. Therefore, the obvious and customary approaches in restoring lost mineral have focused on calcium-containing compositions.

In some embodiments, the novel technology does not include calcium in the remineralization of weakened teeth. In these firstly discussed embodiments, the novel technology pertains to non-calcium agents that may be combined with fluoride for improved remineralization of teeth.

Currently, phosphate may be added in the form of phosphoric acid and sodium phosphate monobasic when coupled with fluoride for the remineralization of enamel. Examples of dental preparations containing fluoride and phosphoric acid include, for instance, COLGATE® PHOS-FLUR® (COLGATE and PHOS-FLUR are registered trademarks of Colgate-Palmolive Company, 300 Park Ave, New York, N.Y. 10022. Reg. Nos. 73636078, 72188106) fluoride gel (pH about 5.1) or acidulated fluoride mouth rinses, which are both low pH formulations comprising phosphoric acids. The pH of acidulated phosphate fluorides can range between 3.0 and 4.5. These formulations typically contain about 0.1M phosphate (about 9,600 ppm phosphate), and are typically comprised of phosphoric acid and sodium phosphate monobasic. These low pH systems typically lead to enhanced fluoride uptake due to simultaneous dissolution of apatite (which dissolves at pH less than 5.5) and corresponding fluoride uptake. Based on the fluoride monograph and commercially marketed acidulated phosphate fluoride formulations, the typical concentration ratios of fluoride to phosphate range from at least 1:5 up to about 1:50. Or, put in other words, the phosphate to fluoride ratios typically range from about 1:50 to about 1:5.

The present novel technology relates to the addition of water-soluble phosphate salts in the absence, or presence, of calcium from about 10 ppm phosphate to about 10,000 ppm phosphate. In contrast to existing wisdom and practice, the instant invention is especially useful when the fluoride content is much greater than phosphate content (such as present in a ratio of about 10:1 more). Also, the system can function independently of the presence of phosphoric acid.

Furthermore, the phosphate salt may be combined with fluoride in the above given amounts (ratios and concentrations) for mineralization of enamel. One benefit of the instant system is that thorough rinsing with water is not required after its application to prevent unwanted tooth mineral dissolution. This contrasts markedly with acidulated phosphate fluoride dental preparations, which must be rinsed away such that the dentition is not continuously damaged by standing acid. Demonstrated benefits of the novel system are detailed in the following examples.

Example 1

A pH cycling regimen was performed to demonstrate the effects of fluoride supplemented with water-soluble potassium dihydrogen phosphate. Six treatment groups were evaluated in this model:
1. distilled water;
2. 0.22% NaF (1,000 ppm F);
3. 0.22% NaF (1,000 ppm F)+0.01% $KH_2PO_4$ (100 ppm $PO_4$) (1:10 P-to-F);
4. 0.22% NaF (1,000 ppm F)+0.07% $KH_2PO_4$ (500 ppm $PO_4$) (1:2 P-to-F);
5. 0.22% NaF (1,000 ppm F)+0.14% $KH_2PO_4$ (1,000 ppm $PO_4$) (1:1 P-to-F); and,
6. 0.22% NaF (1,000 ppm F)+0.71% $KH_2PO_4$ (5,000 ppm $PO_4$) (5:1 P-to-F).

Three millimeter diameter bovine enamel was initially demineralized using a polyacrylic-lactic acid solution, saturated 50% with hydroxyapatite and pH adjusted to 5.0. Baseline surface microhardness measurements were made (Vickers, 200 gF, 15 sec dwell time, four measurements per specimen). Each treatment group had five enamel specimens that were cycled through the model listed below in Table 2 for 10 days.

TABLE 2

Outline of pH cycling model.

| Event | Duration |
| --- | --- |
| Treatment #1 | 1 minute |
| Saliva, pH = 7.0 | 1 hour |
| Treatment #2 | 1 minute |
| Saliva, pH = 7.0 | 1 hour |
| Acid Challenge, pH = 5.0 | 4 hours |
| Saliva, pH = 7.0 | 1 hour |
| Treatment #3 | 1 minute |
| Saliva, pH = 7.0 | 1 hour |
| Treatment #4 | 1 minute |
| Saliva, pH = 7.0 | Overnight |

Interim surface microhardness measurements were made after five days of cycling, and then again after 10 days of cycling. Additionally, subsurface microhardness measurements were also made. The results from these measurements are listed below in Tables 2 and 3, respectively.

TABLE 3

Mean (standard error of the mean) five- and ten-day post surface microhardness recoveries (% SMHR[5] and SMHR[10], respectively) results obtained by Vickers microhardness indents (N = 5).

| Groups | % SMHR[5] | % SMHR[10] |
| --- | --- | --- |
| 0.0% F (control) | −0.6 (0.4) | 0.3 (0.7) |
| 0.22% NaF | 19.4 (4.3) | 21.5 (3.3) |
| 0.22% NaF + 0.01% $KH_2PO_4$ | 34.4 (4.6) | 50.6 (3.2) |
| 0.22% NaF + 0.07% $KH_2PO_4$ | 26.1 (6.9) | 52.7 (2.4) |

TABLE 3-continued

Mean (standard error of the mean) five- and ten-day post surface microhardness recoveries (% SMHR[5] and SMHR[10], respectively) results obtained by Vickers microhardness indents (N = 5).

| Groups | % SMHR[5] | % SMHR[10] |
| --- | --- | --- |
| 0.22% NaF + 0.14% $KH_2PO_4$ | 43.2 (4.6) | 55.2 (3.8) |
| 0.22% NaF + 0.71% $KH_2PO_4$ | 35.5 (3.8) | 47.5 (3.0) |

TABLE 4

Summary relative lesions size results (mean (standard error of the mean)) determined through cross-sectional microhardness (CSMH) measurements made after the 10-day cycling regimen (N = 5 x three measurement lanes).

| Groups | Relative Lesion Size ($\sqrt{KHN} \cdot \mu m$) |
| --- | --- |
| 0.0% F (control) | 522.7 (54.1) |
| 0.22% NaF | 247.1 (38.8) |
| 0.22% NaF + 0.01% $KH_2PO_4$ | 52.2 (35.7) |
| 0.22% NaF + 0.07% $KH_2PO_4$ | 118.0 (51.9) |
| 0.22% NaF + 0.14% $KH_2PO_4$ | 43.5 (34.9) |
| 0.22% NaF + 0.71% $KH_2PO_4$ | 121.5 (29.7) |

When combined with fluoride as shown above, supplementation with 100 ppm phosphate can produce significant surface and subsurface strengthening relative to fluoride alone. Further remineralization is achieved in this calcium-free system when the phosphate weight percent is about ten-fold less than the fluoride weight percent, or in equal concentration of fluoride and phosphate.

Detailed Example 2

A pH cycling regimen was performed in accord with Table 2 to demonstrate the enamel strengthening effects of fluoride supplemented with water-soluble potassium dihydrogen phosphate ($KH_2PO_4$). Six treatment groups were evaluated in this model:
1. 0.0% NaF (distilled water);
2. 0.044% NaF (200 ppm F);
3. 0.044% NaF (200 ppm F)+0.002% $KH_2PO_4$ (20 ppm $PO_4$) (1:10 P-to-F);
4. 0.044% NaF (200 ppm F)+0.01% $KH_2PO_4$ (100 ppm $PO_4$) (1:2 P-to-F);
5. 0.22% NaF (1,000 ppm F); and,
6. 0.22% NaF (1,000 ppm F)+0.002% $KH_2PO_4$ (20 ppm $PO_4$) (1:50 P-to-F).

Interim surface microhardness measurements were made after five days of cycling, and then again after 10 days of cycling. Additionally, subsurface microhardness measurements were also made. The results from these measurements are listed below in Tables 5 and 6, respectively.

TABLE 5

Mean (standard error of the mean) five- and ten-day post surface microhardness recoveries (% SMHR[5] and SMHR[10], respectively) results obtained by Vickers microhardness indents (N = 10).

| Treatment Groups | % SMHR[5] | % SMHR[10] |
| --- | --- | --- |
| 0.0% NaF | 0.6 (0.4) | 0.4 (0.4) |
| 0.044% NaF | 9.8 (1.0) | 27.4 (2.8) |
| 0.044% NaF + 0.002% $KH_2PO_4$ | 13.6 (1.3) | 34.4 (2.2) |
| 0.044% NaF + 0.01% $KH_2PO_4$ | 11.9 (1.5) | 31.2 (3.8) |
| 0.22% NaF | 30.3 (2.6) | 41.1 (3.0) |
| 0.22% NaF + 0.002% $KH_2PO_4$ | 36.3 (1.9) | 52.5 (2.2) |

TABLE 6

Summary relative lesions size results (mean (standard error of the mean)) determined through cross-sectional microhardness (CSMH) measurements made after the 10-day cycling regimen (N = 10 x three measurement lanes).

| Treatment Groups | Relative Lesion Size ($\sqrt{KHN} \cdot \mu m$) |
| --- | --- |
| 0.0% NaF | 517.5 (22.7) |
| 0.044% NaF | 248.0 (33.6) |
| 0.044% NaF + 0.002% $KH_2PO_4$ | 345.6 (30.4) |
| 0.044% NaF + 0.01% $KH_2PO_4$ | 232.8 (24.2) |
| 0.22% NaF | 185.9 (19.1) |
| 0.22% NaF + 0.002% $KH_2PO_4$ | 148.1 (26.2) |

When combined with fluoride as shown in Example 2 above, supplementation with about 0.002% (i.e. 20 ppm) phosphate to 200 or 1,000 ppm fluoride can produce greater surface and subsurface strengthening relative to fluoride alone. Further remineralization can be achieved in this calcium-free system when the phosphate weight percent is at 50-fold less than the fluoride weight percent.

Detailed Example 3

A pH cycling regimen was performed to demonstrate the effects water-soluble potassium dihydrogen phosphate ($KH_2PO_4$) in the absence of fluoride. Three treatment groups were evaluated in this model:

1. 0.0% $KH_2PO_4$ (distilled water);
2. 0.14% $KH_2PO_4$ (1,000 ppm $PO_4$); and,
3. 0.71% $KH_2PO_4$ (5,000 ppm $PO_4$).

Three millimeter diameter bovine enamel was initially demineralized using a polyacrylic-lactic acid solution, saturated 50% with hydroxyapatite and pH adjusted to 5.0. Baseline surface microhardness measurements were made (Vickers, 200 gF, 15 sec dwell time, four measurements per specimen). Each treatment group had five enamel specimens that were cycled through the model listed below in Table 7 for 10 days.

TABLE 7

Outline of pH cycling.

| Event | Duration |
| --- | --- |
| Simulated Saliva, pH = 7.0 | 1 hour |
| Acid Challenge #1, pH = 5.0 | 30 minutes |
| Simulated Saliva, pH = 7.0 | 1 hour |
| Treatment #1 | 9 minutes |
| Simulated Saliva, pH = 7.0 | 1 hour |
| Acid Challenge #2, pH = 5.0 | 30 minutes |
| Simulated Saliva, pH = 7.0 | 1 hour |
| Treatment #2 | 9 minutes |
| Simulated Saliva*, pH = 7.0 | 1 hour |
| Acid Challenge #3, pH = 5.0 | 30 minutes |
| Simulated Saliva, pH = 7.0 | 1 hour |
| Treatment #3 | 9 minutes |
| Simulated Saliva, pH = 7.0 | Overnight |

After five and ten days of cycling, surface and subsurface microhardness measurements were made. The results from these measurements are listed below in Tables 8 and 9, respectively.

TABLE 8

Mean (standard error of the mean) five- and ten-day post surface microhardness recoveries (% $SMHR^5$ and $SMHR^{10}$, respectively) results obtained by Vickers microhardness indents (N = 5).

| Treatment Groups | % $SMHR^5$ | % $SMHR^{10}$ |
| --- | --- | --- |
| 0.0% $KH_2PO_4$ | 4.6 (0.8) | 7.8 (0.2) |
| 0.14% $KH_2PO_4$ | 6.4 (1.3) | 12.0 (3.5) |
| 0.71% $KH_2PO_4$ | 5.6 (1.6) | 6.2 (2.0) |

TABLE 9

Summary relative lesions size results (mean (standard error of the mean)) determined through cross-sectional microhardness (CSMH) measurements made after the 10-day cycling regimen (N = 5 x three measurement lanes).

| Treatment Groups | Relative Lesion Size ($\sqrt{KHN} \cdot \mu m$) |
| --- | --- |
| 0.0% $KH_2PO_4$ | 327.6 (30.5) |
| 0.14% $KH_2PO_4$ | 205.7 (35.9) |
| 0.71% $KH_2PO_4$ | 293.9 (59.6) |

When combined with fluoride as shown in Example 3 above, supplementation with about 1,000 ppm phosphate in the absence of fluoride can produce greater surface and subsubsurface strengthening relative to fluoride alone.

Detailed Example 4

A pH cycling regimen was performed to demonstrate the effects water-soluble potassium dihydrogen phosphate ($KH_2PO_4$) in the absence of fluoride. Two treatment groups were evaluated in this model:

1. 0.0% $KH_2PO_4$ (distilled water); and,
2. 0.07% $KH_2PO_4$ (500 ppm $PO_4$).

Three millimeter diameter bovine enamel was initially demineralized using a polyacrylic-lactic acid solution, saturated 50% with hydroxyapatite and pH adjusted to 5.0. Baseline surface microhardness measurements were made (Vickers, 200 gF, 15 sec dwell time, four measurements per specimen). Each treatment group had five enamel specimens that were cycled through the model listed in Table 7 for 10 days.

After five and ten days of cycling, surface and subsurface microhardness measurements were made. The results from these measurements are listed below in Tables 10 and 11, respectively.

TABLE 10

Mean (standard error of the mean) five- and ten-day post surface microhardness recoveries (% $SMHR^5$ and $SMHR^{10}$, respectively) results obtained by Vickers microhardness indents (N = 5).

| Treatment Groups | % $SMHR^5$ | % $SMHR^{10}$ |
| --- | --- | --- |
| 0.0% $KH_2PO_4$ | 6.5 (1.7) | 11.7 (2.9) |
| 0.07% $KH_2PO_4$ | 15.1 (2.0) | 22.1 (1.8) |

TABLE 11

Summary relative lesions size results (mean (standard error of the mean)) determined through cross-sectional microhardness (CSMH) measurements made after the 10-day cycling regimen (N = 5 x three measurement lanes).

| Treatment Groups | Relative Lesion Size ($\sqrt{KHN} \cdot \mu m$) |
|---|---|
| 0.0% $KH_2PO_4$ | 399.1 (22.6) |
| 0.07% $KH_2PO_4$ | 300.9 (36.1) |

When combined with fluoride as shown in Example 4 above, supplementation with about 500 ppm phosphate can produce greater surface and subsurface strengthening relative to fluoride alone.

Phosphate, without fluoride, is typically present in aqueous solution in concentrations of between about 10 ppm and about 10,000 ppm, more typically between about 100 ppm and about 5000 ppm, and still more typically between about 200 ppm and about 1000 ppm. With fluoride present, phosphate is typically present in concentrations of between about 50 ppm and about 10,000 ppm, more typically between about 500 ppm and about 5000 ppm, and still more typically between about 500 ppm and about 2500 ppm. The fluoride-to-phosphate ratios are typically between about 1:5 and about 20:1, more typically between about 1:1 and about 10:1.

In some embodiments of the novel technology, phosphate and calcium may be derived from separate salts and then combined to strengthen or fortify dentition. Typically, the phosphate and calcium salts are combined in an aqueous solution within the oral cavity wherein the phosphate and calcium components both exhibit high water solubility. While it has been noted previously that a phosphate solution that is calcium-free may aide in the remineralization of dentition, the addition of a separate calcium salt to the phosphate containing salts for the purposes of dentition strengthening or fortification may be desired.

In some embodiments, separate phosphate salts (such as potassium phosphate, sodium phosphate, and the like) may be suspended with separate calcium salts in a semi-solid, gelatinous delivery and/or gummy matrix. Typically, the phosphate salts and calcium salts are derived separately in order to generate advantageous tooth strengthening benefits.

In one embodiment, very soluble and physically separate phosphate and calcium salts are present in a gelatinous or gummy matrix for combination in an aqueous solution within the oral cavity. The phosphate concentration is typically between about 100 to 10,000 ppm, and more typically between about 100 and 500 ppm. The ratio of phosphate to calcium present in an aqueous solution is typically at least 1:1, and still more typically at least 2:1, however, the phosphate to calcium ratio may be 3:1 or even as much as 5:1. Typically, the solubility of the phosphate salt is 1 gram per 100 g of water at 20° C. to about 93 grams per 100 grams of water at 20° C. Typically, the solubility of the calcium salt is between about 1 gram per 100 grams of water at 20° C. to about 75 grams per 100 grams of water at 20° C.

In some embodiments, in addition to the phosphate and calcium salts, other nutrients may be dispersed in the gummy or gelatinous matrix. For example, vitamin D may be added as a supplement to modulate bacterial activity in the mouth and provide additional anti-caries efficacy. Vitamin D may be added alone or in combination with calcium and/or phosphate salts. A combination typically includes about 10 micrograms of vitamin D, however, the amount of vitamin D may be varied as desired. Further, fluoride may be added along with phosphate salts alone, calcium and phosphate salts, or calcium and phosphate salts with other nutrients.

In some embodiments, the phosphate and calcium salts may be combined with other vitamins or minerals in a gummy or gelatinous delivery matrix. The delivery matrix may be combined with other active or non-active ingredients found typically found in gummies, a gummy vitamin or like gelatinous substances.

Table 12 illustrates the active dentition strengthening ingredients typically found in a gummy embodiment of the present novel technology.

TABLE 12

Active Ingredients for Tooth Strengthening Gummy or Gelatin Matrix

| Active Ingredient | Amount |
|---|---|
| Vitamin D (cholecalciferol) | 400 IU (or 10 mcg) |
| Phosphorous | 13 mg |
| Potassium | 3.8 mg |
| Calcium | 4.5 mg |
| Chloride | 7.8 mg |

In some embodiments, the highly soluble phosphate typically contributes to the prevention of the formation of tartar and/or calculus.

In another embodiment, highly soluble separate calcium and phosphate precursory (salts) are combined in a mint, chocolate or other foodstuff or supplement. The high-solubility of the calcium and phosphate sources in aqueous solution may allow for their incorporation into solid foods, gelatins, gels, pastes, rinses, and the like.

In operation, predetermined amounts of separate phosphate and calcium salts may be dispersed in a semi-solid comestible matrix, such as a gummy, gelatin, chewing gum, or the like. When the semi-solid comestible matrix is chewed, the phosphate salts and calcium salts combine with saliva to define an aqueous solution. The phosphate-calcium aqueous solution is then available to penetrate dentition and remineralize and/or strengthen the dentition. The semi-solid comestible matrix may include other vitamins and minerals in varying concentrations, as may be desired. The phosphate and calcium precursor compounds are typically very water soluble, and are more typically soluble in ranges of 1 gram per 100 g of water at 20° C. to about 93 grams per 100 grams of water at 20° C. for the phosphate precursor and between about 1 gram per 100 grams of water at 20° C. to about 75 grams per 100 grams of water at 20° C. for the calcium precursor and still more typically present in sufficient amounts in the comestible matrix to yield solutions with a phosphate concentration between about 10 ppm to about 10,000 ppm in the oral cavity.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

I claim:

1. A dentition strengthening delivery system comprising:
   a gelatinous semi-solid comestible matrix;
   a first phosphate salt suspended with a second calcium salt in the matrix;
   wherein the phosphate-to-calcium ratio in the semi-solid comestible matrix is between 3:1 and 5:1;
   wherein the first phosphate salt is different from the second calcium salt;
   wherein the solubility of the phosphate salt in the semi-solid comestible matrix is between about 1 g/100 g of water to about 93 g/100 g of water at 20° C.; and
   wherein the solubility of the calcium salt in the semi-solid comestible matrix is between about 1 g/100 g of water to about 75 g/100 g of water at 20° C.;
   wherein the first phosphate salt and the second calcium salt comprise less than 5 weight percent of the semi-solid comestible matrix; and
   wherein the semi-solid comestible matrix has a phosphate concentration of about 100 ppm.

2. The dentition strengthening system of claim 1, further comprising a predetermined amount of vitamin D suspended in the matrix.

3. The dentition strengthening system of claim 1, wherein the semi-solid comestible matrix is a mint.

4. The dentition strengthening system of claim 1, wherein the phosphate salt is potassium phosphate monobasic.

5. The dentition strengthening system of claim 1, wherein the calcium salt is calcium chloride.

6. A dentition fortifying delivery system comprising:
   a gummy matrix;
   vitamin D distributed throughout the gummy matrix;
   phosphate monobasic salt distributed throughout the gummy matrix;
   calcium chloride distributed throughout the gummy matrix;
   wherein the phosphate concentration is about 100 ppm;
   wherein the concentration of vitamin D is between about 1 and 20 mcg;
   wherein the ratio of phosphate to calcium is between 3:1 and 5:1; and
   wherein the phosphate monobasic salt and calcium chloride amount to less than two percent of the dentition fortifying system.

7. The dentition fortifying system of claim 6, wherein the solubility of the phosphate salt is between about 1 g/100 g of water to about 93 g/100 g of water at 20° C.

8. The dentition fortifying system of claim 6, the solubility of the calcium salt is between about 1 g/100 g of water to about 75 g/100 g of water at 20° C.

9. A dentition reinforcing oral delivery system comprising:
   a comestible matrix;
   a first phosphate salt evenly dispersed throughout the matrix;
   a second, different calcium salt evenly dispersed throughout the matrix;
   wherein the phosphate-to-calcium ratio in the matrix is at least about 3:1;
   wherein the phosphate concentration is about 100 ppm; and
   wherein the comestible matrix is at least ninety-nine weight percent of the dentition reinforcing oral delivery system.

* * * * *